United States Patent [19]

Bremer et al.

[11] 4,002,650
[45] Jan. 11, 1977

[54] PREPARATION OF MALEIC ANHYDRIDE FROM n-BUTANE

[75] Inventors: Noel J. Bremer, Stow; Ernest C. Milberger, Solon; Serge R. Dolhyj, Parma, all of Ohio

[73] Assignee: The Standard Oil Co. (Ohio), Cleveland, Ohio

[22] Filed: Dec. 10, 1973

[21] Appl. No.: 423,032

[52] U.S. Cl. .................................. 260/346.8 A
[51] Int. Cl.² ................................ C07D 307/60
[58] Field of Search .......................... 260/346.8

[56] References Cited

UNITED STATES PATENTS

| | | | |
|---|---|---|---|
| 2,294,130 | 8/1942 | Porter | 260/346.8 |
| 2,625,519 | 1/1953 | Hartig | 260/346.8 |
| 3,074,969 | 1/1963 | Kerr et al. | 260/346.8 |
| 3,867,411 | 2/1975 | Raffelson et al. | 260/346.8 |
| 3,888,886 | 6/1975 | Young et al. | 260/346.8 |

FOREIGN PATENTS OR APPLICATIONS

| | | | |
|---|---|---|---|
| 1,601,955 | 10/1970 | France | 260/346.8 |
| 2,219,603 | 11/1972 | Germany | 260/346.8 |

*Primary Examiner*—Henry R. Jiles
*Assistant Examiner*—Bernard Dentz
*Attorney, Agent, or Firm*—Herbert D. Knudsen; Larry W. Evans; Gwenetta D. Hill

[57] ABSTRACT

Catalysts containing the oxides of vanadium, phosphorus and uranium have been found to be especially effective in the oxidation of n-butane, n-butenes and butadiene with molecular oxygen in the vapor phase to yield maleic anhydride. The reaction with n-butane gives an especially pure product in high yield.

1 Claim, No Drawings

PREPARATION OF MALEIC ANHYDRIDE FROM n-BUTANE

BACKGROUND OF THE INVENTION

Catalysts of vanadium and phosphorus have been used in the production of maleic anhydride. However, the low yields obtained using these catalysts have spurred a search for better catalysts. The present invention is a result of this search for new catalysts in this reaction.

SUMMARY OF THE INVENTION

It has been discovered in the process for the production of maleic anhydride by the oxidation of n-butane, n-butenes, butadiene or mixture thereof with molecular oxygen in the vapor phase in the presence of a catalyst, the improvement comprising using as the catalyst a catalyst containing the oxides of at least vanadium, phosphorus and uranium. The process of the present invention is especially effective for the production of very pure maleic anhydride from n-butane in high yields. Moreover, the catalysts of the invention have long effective lives.

The central aspect of the present invention is the catalyst. As noted, the catalyst of the invention contains at least the oxides of vanadium, phosphorus and uranium. This base catalyst may be optionally promoted with metal oxides. Suitable metal oxides include but are not limited to those of the lanthanide series, Group VIII, Groups IA and Group IIA.

Preferred catalysts are described by the following empirical formula $V_a P_b U_c O_x$ wherein a and b are 0.1 to 10;

c is 0.01 to 5; and x is the number of oxygens to satisfy the valence requirements of the other elements present.

Catalysts of special interest within this formula are described when a and b are 0.5 to 3 and c is 0.1 to 0.5.

The catalysts may be prepared by a number of known methods. The catalysts are conveniently prepared by digesting oxides or salts of the various ingredients of the catalyst in concentrated hydrochloric acid. Other methods such as combining the oxides or nitrates, are also acceptable. The most preferred preparation is described in the Specific Embodiment.

The catalyst may be used alone or a support could be employed. Suitable supports include silica, alumina, Alundum, silicon carbide, boron phosphate, zirconia and the like. The catalyst is conveniently used in a fixed-bed reactor using tablets, pellets or the like or in a fluid-bed reactor using a catalyst preferably having a particle size of less than about 300 microns.

The process for preparing maleic anhydride using the catalysts of the invention is known. The process involves reacting the hydrocarbon with molecular oxygen in the vapor phase in the presence of the catalyst.

The hydrocarbon reacted may be n-butane, n-butenes, butadiene or mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of the hydrocarbon to molecular oxygen may range from about 2 to about 30 moles of oxygen per mole of hydrocarbon. The higher oxygen ratios are associated with fixed-bed reactors and are used to avoid the explosive range of the reactants. Preferred oxygen ratios are about 4 to about 20 moles per mole of hydrocarbon.

The reaction temperature may vary widely and is dependent upon the particular hydrocarbon and catalyst employed. Suitably, a temperature within the range of about 350° to about 600° C. gives the best results. The reaction can be conducted at atmospheric, superatmospheric or subatmospheric pressure. The contact time may range from less than a second to ten seconds or more. These reaction parameters are not of paramount importance because these conditions are known and are not the novelty of the present invention.

SPECIFIC EMBODIMENT

A catalyst of the formula  $V_1P_{1.15}U_{0.2}O_x$ was prepared as follows: 33.6 g. of $V_2O_5$ was digested in 438 cc. of concentrated HCl, 31.3 g. of $UO_2(C_2H_3O_2)_2 \cdot 2H_2O$ was added and refluxed for one hour. To this was added 48.9 g. of 85% $H_3PO_4$, and the mixture was refluxed for two hours. The mixture was evaporated at atmospheric pressure on a hot plate and dried overnight at 110° C. The catalyst was ground and screened to give a 10 by 30 mesh fraction. The reactor was constructed of a 1.02 cm. inside diameter stainless steel tube. A portion of the catalyst fraction was charged to the 20 cc. reaction zone of the reactor. The catalyst was activated by heating in an air flow at 482° C. for 16 hours.

After the activation, an n-butane/air feed of 1/100 was passed over the catalyst at 482° C. for a contact time of 1.35 seconds. After 122 hours of continuous operation, the n-butane/air ratio was changed to 1/70 using the same reaction conditions.

The results of the experiments were analyzed by acid titration of the product from a given amount of feed. Product samples were also analyzed by potentiometric titration and found to be pure maleic anhydride even though only an air condensation of the maleic anhydride was used.

The results are shown in the following table. The results are stated as follows:

$$\text{Single Pass Yield} = \frac{\text{moles of maleic anhydride formed}}{\text{moles of butane fed}} \times 100$$

$$\text{Weight Percent Yield} = \frac{\text{weight of maleic anhydride formed}}{\text{weight of butane fed}} \times 100$$

Table

Maleic Anhydride from Butane

| Time on Stream, Hrs. | Yields, % Single Pass | Weight Percent |
|---|---|---|
| 8 | 50.0 | 84.5 |
| 107 | 47.4 | 80.1 |
| 126 | 49.0 | 82.8 |

In the same manner, other catalysts containing different amounts of vanadium, phosphorus and uranium are used to prepare maleic anhydride from n-butane.

Also in the same manner, various catalysts of the invention are promoted with elements, such as nickel, cerium, antimony, rubidium or magnesium, to give desirable yields of maleic anhydride from n-butane, n-butenes or butadiene.

We claim:

1. In the process for the production of maleic anhydride by the oxidation of n-butane with molecular oxygen in the vapor phase at a reaction temperature of 350°–600° C. in the presence of a catalyst of the formula $$V_a P_b U_c O_x$$

wherein a and b are 0.5 to 3;
c is 0.1 to 0.5; and
x is the number of oxygens to satisfy the valence requirements of the other elements present.

* * * * *